United States Patent [19]

Seijiro et al.

[11] Patent Number: 4,654,304
[45] Date of Patent: Mar. 31, 1987

[54] COMPOSITION FOR CELL CULTIVATION, PRODUCTION AND USE THEREOF

[75] Inventors: Sasai Seijiro, Hikari; Fujimoto Tadanobu, Kumage; Tsukamoto Kyozo, Suita, all of Japan

[73] Assignee: Takeda Chemical Industries, Ltd., Osaka, Japan

[21] Appl. No.: 687,596

[22] Filed: Dec. 31, 1984

[30] Foreign Application Priority Data

Jan. 7, 1984 [JP] Japan .................................... 59-521

[51] Int. Cl.$^4$ .......................... C12N 5/00; C12R 1/91; C07K 15/06
[52] U.S. Cl. .................................... 435/240; 435/800; 435/948; 530/380
[58] Field of Search ............... 435/240, 241, 800, 948; 260/112 B; 530/380

[56] References Cited

U.S. PATENT DOCUMENTS

| | | | |
|---|---|---|---|
| 3,128,228 | 4/1964 | Michl | 435/240 |
| 4,038,139 | 7/1977 | Birch | 435/241 |
| 4,248,971 | 2/1981 | Youssef | 435/253 |
| 4,452,893 | 6/1984 | Ng et al. | 435/240 |
| 4,473,647 | 9/1984 | Carpenter et al. | 435/240 |
| 4,560,655 | 12/1985 | Baker | 435/241 |

FOREIGN PATENT DOCUMENTS 0141782  8/1983  Japan .................................... 435/240

OTHER PUBLICATIONS

Frobisher, Hinsdill, Crabtree and Goodheat, *Fundamentals of Microbiology* (9th ed) W. B. Saunders Co., Philadelphia, 1974, p. 313.
Central Patents Index, Abstracts Journal, Section D, No. 80313V/46, The Abstract of Dutch Patent Publication (laid open) No. 5707/1974.
Central Patents Index, Abstracts Journal, Section B, No. 49128E/24, The Abstract of Japanese Patent Publication (laid open) No. 74085/1982.
Central Patents Index, Abstract Journal, Section B, No. 79664E/38, The Abstract of Japanese Patent Publication (laid open) No. 129687/1982.

*Primary Examiner*—Thomas G. Wiseman
*Assistant Examiner*—Karen Maurey
*Attorney, Agent, or Firm*—David G. Conlin; Ernest V. Linek

[57] ABSTRACT

The present inventiona is directed to a mammalian serum-originated growth factor-containing composition useful in cell cultivation. The composition of the present invention is substantially free of active microorganisms and other harmful substances which would otherwise interfere with cell cultivation. Preferably the composition of the present invention is totally free of contaminant microorganisms, i.e., is sterile.

The present invention is also directed to a method of producing the composition of the invention. One step of this method comprises the inactivation of any contaminant microorganisms present in the starting serum. Another step comprises the salting out and desalting of the starting serum to obtain a fraction of the serum which contains the desired cell growth factor. Either step may be conducted first.

Finally the present invention provides a medium for cell cultivation which medium contains the present composition together with a basal medium, as well as a cultivation composition which contains the medium and the cells.

15 Claims, 2 Drawing Figures

4,654,304

COMPOSITION FOR CELL CULTIVATION, PRODUCTION AND USE THEREOF

FIELD OF THE INVENTION

This invention relates to a composition for cell cultivation, production and use thereof.

BACKGROUND OF THE INVENTION

For the cultivation of animal cells or animal tissues, it has been found that the addition of animal serum, as a cell growth factor, to the basal medium is essential. With the advances in recent years in cytology and immunology as well as in large-scale animal cell culture techniques, the demand for serum is markedly increasing.

Important criteria in using animal sera as a cell growth additive include the species and age of the animals whence the sera is derived, as well as any presence of contaminant microorganisms, cytotoxic substances, antibodies, growth-inhibiting substances, and the like. The cost and labor involved in obtaining such information are considerable and, moreover, the number or quantity of serum lots which can meet the high purity requirements is limited in many cases.

Among various sera, fetal bovine serum and neonatal bovine serum are being used with increasing frequency because of their superiority to other sera with respect to their cell growth promoting effect and their low content of undesired substances, among others. However, current problems with such sera include the difficulty in obtaining them, especially due to limited source availability and high costs.

In view of these circumstances, the present inventors conducted intensive studies and have now created a composition for cell cultivation which has excellent cell growth promoting effect and which contains no significant amounts of useless or harmful substances. The composition may be produced, with ease and at low cost, by using not only fetal or neonatal bovine serum as the starting material, but also adult bovine serum, or serum of some other animal species which is readily available for large quantity blood collection, such as horse, sheep or swine.

SUMMARY OF THE INVENTION

The present invention provides a mammalian serum-originated growth factor-containing composition for cell cultivation, the composition being substantially free of active microorganisms and other harmful substances and preferably being totally free of active microorganism (i.e., sterile. The present invention also provides a method of producing the composition which comprises subjecting a mammalian serum to treatments comprising a step of inactivating contaminated microorganisms and a step of salting out and desalting to obtain a fraction which contains cell growth factor and is free of other harmful substances. Finally, the present invention provides a medium for cell cultivation which contains said composition together with a basal medium, and a cultivation composition which contains the medium and cells.

The mammalian serum to be used in the practice of the invention may be derived from any species, although bovine, equine, ovine and swine sera, among others, may be advantageously used for reasons of their ready availability.

The mammals from which the serum is derived may be at any age, e.g., fetuses, newborns, youngs or adults. That sera of adult animals can also be used is a characteristic feature of the method of the present invention.

BRIEF DESCRIPTION OF THE DRAWINGS

In the accompanying drawings.

DETAILED DESCRIPTION OF THE PREFERRED EMBODIMENTS

Figure 1:
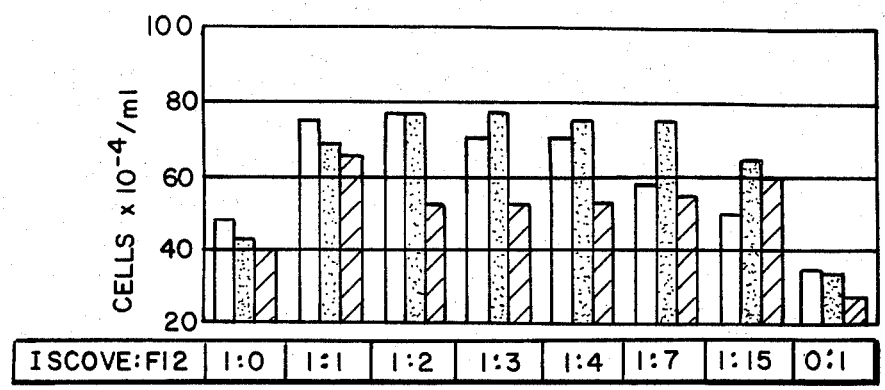
FIG. 1 shows the cell proliferation promoting activity of Iscove/F12 mixed medium as described in Example 6 as a function of the mixing ratio (    : NGE-44 cells;    : CEA cells;    : I-63 cells).

The first step of the method of the present invention, i.e., the step of inactivating contamined microorganisms, is conducted for the purpose of inactivating animal-derived microorganisms as well as microorganisms possibly coming into the blood or serum, either at the time of, or sometime after the blood collection. Since such microorganisms are generally viruses, mycoplasmas and the like, such treatment is preferably carried out by adding an inactivating agent highly capable of inactivating viruses, mycoplasmas and so on but poorly capable of affecting cell growth promoting substances in serum. Effective inactivating agents include $C_2$ to $C_4$ alkenyl oxides such as ethylene oxide and propylene oxide and dialdehydes such as glyoxal ($C_2$) and glutaraldehyde ($C_5$) and, among the effective agents, ethylene oxide, particularly ethylene oxide in liquid form, is especially advantageous from the viewpoints of inactivating capacity and influence on growth promoting substances, among others.

When liquid ethylene oxide is used, it is added in an amount of about 0.1–5 percent by volume, preferably about 1–3 percent by volume and the serum is allowed to stand at about 0° to 30° C., preferably about 5° C. to room temperature, for about 1–7 days, preferably about 2–5 days, during which inactivation is effected. The above conditions are also applicable to the cases where other inactivating agents are used. Generally, no particular treatment is required for the removal of the inactivating agent added for the purpose of inactivating contaminant microorganisms. Said agent is eliminated during standing or during other procedures involved in the normal handling of the growth medium. If desired, however, a positive measure for removal of the inactivating agent, such as dialysis, may be taken in a manner known per se in the art.

The second step of the method of the present invention, i.e., the step of salting out and desalting in accordance with the invention are carried out, for instance, in the following manner:

For salting out, a salt, for example an inorganic salt, is used. The inorganic salt includes, among others, ammonium salts (ammonium sulfate, ammonium chloride, etc.), sodium salts (sodium chloride, etc.) and potassium salts (potassium carbonate). Among these, preferred are ammonium salts, in particular ammonium sulfate.

In the practice of the method of the present invention, the salting out is performed in a conventional manner. Thus, the raw material serum or the serum from the above-mentioned step of inactivating contaminant microorganisms is dissolved or suspended in a solvent (e.g., water, ethanol, aqueous ethanol), and the salt is added thereto until a predetermined lower limit concentration of the salt is reached. The resulting precipitate is removed. To the supernatant, there is further added a salt to a predetermined upper limit concentration and the resulting precipitate is collected. This is the desired fraction.

In a preferred embodiment, i.e., when ammonium sulfate is used as the salt, the salting out is preferably conducted by using said salt at a lower limit concentration of not less than 40% saturation, preferably not less than 50% saturation, most preferably 55% saturation, and at an upper limit concentration of not higher than 80% saturation, most preferably 70% saturation. When other salts are used, the salting out can be effected at predetermined concentrations corresponding to the above-mentioned ammonium sulfate concentrations. The precipitate can be separated from the supernatant advantageously by centrifugation, for instance.

The precipitate thus obtained is dissolved in physiological saline, for instance, and desalted by procedures know per se, e.g., by dialysis or ultrafiltration.

Dialysis may be carried out in a conventional manner, for example, by using a membrane dialyzer. Ultrafiltration may likewise be effected in a conventional manner, e.g., by filtration under pressure using an ultrafiltration membrane permeable to substances not higher than 1,000 in molecular weight.

The thus-obtained composition for cell cultivation is generally adjusted to a concentration of from about 20 to 80 mg/ml with physiological saline or the like, followed by bacterial filtration using a membrane filter or the like and, as necessary, further by freezing or lyophilization. Thereafter, the composition can be stored.

In producing the composition for cell cultivation in accordance with the present invention, the step of inactivating contaminant microorganisms can precede or follow the steps of salting out and desalting of the composition.

The composition of the present invention contains a salting-out fraction corresponding to the ammonium sulfate concentration range of 40-80% saturation, which fraction is preferably soluble at the concentration of not less than 40% saturation, preferably not less than 55% saturation, and is insoluble at the concentration of not higher than 80% saturation, preferably not higher than 70% saturation of inorganic salt solution, all of these values being in terms of the preferred embodiment, i.e., sulfate solution. The composition of the present invention is free of harmful substances such as cytotoxic substances and growth inhibiting substances. Said composition is also free of useless substances which are otherwise contained in mammalian serum such as immunoglobulins. The composition of the present invention and contains proteins in the molecular weight range of from 60,000 to 80,000, mostly albumin. As compared with the bovine serum albumin of the prior art, the present composition has good cell growth promoting effect in a greater number of cell species, especially animal cell species. Furthermore, the composition of the present invention can also be used for the passaging of animal cells in tissue culture. The composition for cell cultivation of the present invention is highly sterile. Use of the term "highly sterile" means that the present composition is free of filtrable microorganisms, the contamination with which has been a matter of concern in the prior art of serum preparation, and can be handled in safety. Moreover, said composition is at least comparable in its cell growth promoting effect to various known animal sera, such as fetal or neonatal bovine serum, and bovine serum albumin, and said composition can be used advantageously in culturing various cells, especially animal cells such as myelomas, hybridomas, monolayer cells and other animal cells. In such use, said composition can be added to a basal medium in a concentration of 1-10 mg/ml either alone or in admixture with trace growth promoting substances such as insulin.

Most monolayer or attached cultured cells can grow to a sufficient extent in a basal medium plus the present composition alone. With most myeloma cells, a satisfactory extent of cell proliferation can be achieved when said composition is used in admixture with trace growth promoting substances. Animal cell subculture using a medium containing the present composition is also possible.

The basal medium to which the composition is added may be a single medium or a mixed medium containing from 2 to 4, preferably 2 basal media, for example Iscove/F12, Iscove/Serumless Medium, F12/Serumless Medium, or alpha-MEM/Serumless Medium. The ratios(V/V), for example, of two basal media are in the range of 1:1-1:15.

By using the medium of the present invention containing the composition for cell cultivation of the present invention together with a basal medium, an excellent cell proliferation promoting effect is attained, not only in stationary culture, but also in roller bottle culture.

The basal media described in the present specification are publicly available. The following is a list of reference works directed to such media, with both the abbreviated and full names thereof identified:

Iscove: Iscove's medium [J. Exp. Med., 147, 923 (1978)]
F12: Ham's F12 medium [P.N.A.S.(USA), 53, 288 (1965)]
Serumless Medium:
  Gibco's Serumless Medium
  [P.S.E.B.M., 104, 252 (1960)]
alpha-MEM: MEM alpha medium [Nature, 230, 310 (1971)]
DME: Dulbecco's modified Eagle Medium [Virology, 8, 396 (1959)]

The following examples further illustrate the present invention. It is to be noted however that they are by no means limitative of the scope of this invention.

EXAMPLE 1

(Selective separation of effective fraction)

Calf serum was fractionated using ammonium sulfate and each fraction was examined for cell growth promoting effect. Thus, the salting out was performed in a conventional manner and salted-out fractions corresponding to the stepwise ammonium sulfate concentration ranges of 0-52%, 52-57%, 57-62%, 62-67%, 67-72% and 72-80% saturation were collected. Each precipitate fraction was dissolved in physiological saline and dialyzed against physiological saline.

After bacterial filtration using a membrane filter (Mirex-GV, 0.22 μm; Millipore), each dialyzate was added to a 1:1 mixture of DME medium (Nippon Suisan) and F12 medium (Flow) (hereinafter referred to as DME/F12), together with four trace growth promoting substances, namely 10 μg/ml insulin (Sigma), 20 μg/ml transferrin (Green Cross), 2 μM ethanolamine (Wako Pure Chemical) and $2.5\times10^{-6}$M sodium selenate (Wako Pure Chemical). [The mixed additive consisting of the above trace growth promoting substances at the respective indicated concentrations is hereinafter referred to as ITES; Murakami et al., Proceedings of the National Academy of Sciences USA, 79, 1158–1162 (1982)]. The media thus prepared were comparatively examined for cell proliferation rate. As the controls, there were used three groups in which (i) the serum before salting out, (ii) fetal bovine serum (5 mg/ml), and (iii) bovine serum albumin (5 mg/ml) were respectively added. The cells used were NGE-41 cells obtained by cloning U266 cells [IgE-producing human myeloma cells; Journal of Clinical and Experimental Immunology, 7, 477 (1970)], and anti-human IgE antibody-producing hybridoma I-63 cells (cf. Japanese Patent Unexamined Publication No. 96028/1983). Each medium prepared was distributed in 1 ml/well portions into the wells of a 24-well multidish. To each well, there was added 0.1 ml of a NGE-41 or I-63 cell suspension ($5\times10^5$ to $1.5\times10^6$ cells/ml). After 4–7 days of incubation in a 5% $CO_2$ incubator at 37° C., the cells in each well were counted using a Coulter counter (Nippon Kagaku Kikai). The results thus obtained are summarized in Table 1. The cell growth promoting effect was expressed in terms of cell proliferation rate (cell count after incubation÷cell count at start of incubation).

EXAMPLE 2

(Search for cell growth promoting substances in each animal serum)

With the purpose of discovering further serum sources, neonatal bovine serum, calf serum and adult bovine serum as well as equine and ovine sera were also made subjects of investigation. For each serum species, in the same manner as in Example 1, the serum before salting out and an ammonium sulfate-salted out fraction were added either alone or in combination with ITES and examined for growth promoting effect in each cell line. The results thus obtained are summarized in Table 2.

Based on the results of Example 1, fetal bovine serum, neonatal bovine serum, calf serum, adult bovine serum, equine serum and ovine serum were each fractionated by 45–80% or 57–70% ammonium sulfate saturation and each fraction salted out was dialyzed against physiological saline and then filtered for removal of bacteria. For each serum species, the serum before salting out and the ammonium sulfate-salted out fraction were added to DME/F12 medium at a concentration, as protein, of 5 mg/ml (for myelomas) or to MEM medium (Nissui Seiyaku) at a concentration of 3 mg/ml (for monolayer cells), in each case either alone or in combination with ITES, and examined for cell growth promoting effect in each cell line as expressed in terms of cell proliferation rate. The cell lines used as myelomas

TABLE 1

| | | Calf serum | Ammonium sulfate-salted out fractions from calf serum % saturation | | | | | | Fetal bovine serum | Bovine serum albumin |
|---|---|---|---|---|---|---|---|---|---|---|
| | | | 0–52 | 52–57 | 57–62 | 62–67 | 67–72 | 72–80 | | |
| amount added (mg/ml) | | 7.0 | 5.0 | 0.8 | 3.0 | 5.0 | 3.4 | 0.6 | 5.0 | 5.0 |
| NGE-41 cell line | | $(5.6)^{*1}$ | | | (2.2) | (4.8) | (3.8) | | | |
| ITES | − | 3.8 (Death) | 1.3 | 2.1 | 4.6 (5.5) | 1.8 (1.9) | 1.3 (1.6) | 1.4 | 7.3 | 3.0 |
| | + | 5.6 (Death) | 1.3 | 4.3 | 5.9 (6.8) | 5.1 (5.9) | 3.5 (2.3) | 1.4 | — | 4.0 |
| I-63 cell line | | | | | | | | | | |
| ITES | − | 13.6 (Death) | 1.0 | 2.0 | 8.5 (5.7) | 5.5 (5.1) | 4.4 (3.3) | 1.3 | 16.0 | 3.0 |
| | + | 14.3 (Death) | 1.2 | 5.1 | 9.3 (6.6) | 9.5 (9.2) | 9.9 (6.4) | 1.3 | — | 7.0 |

The values in the table each indicates the cell proliferation rate (cell count after incubation/cell count at start of incubation).
*1 The data in the parentheses are for the cases where a calf serum showing cytotoxicity was used.

When added alone, the salted out fraction at 57–62% ammonium sulfate saturation gave a medium proliferation rate in NGE-41 cells, and those at 57–62% and 62–67% saturation each gave a medium proliferation rate in I-63 cells when compared with the proliferation obtained with BSA. When added together with ITES, those at 57–62% and 62–67% saturation gave considerably high cell proliferation rates in NGE-41 cells whereas, in I-63 cells, those at 57–62%, 62–67% and 67–72% saturation gave fairly high proliferation rates. These high cell proliferation rates, though yet inferior to those attainable with fetal bovine serum, indicate that the fractions mentioned above can be used to satisfaction. The fractions were superior in cell proliferation rate to bovine serum albumin hitherto in use. When a calf serum showing cytotoxicity was subjected to salting out with ammonium sulfate, the cytotoxicity was eliminated.

were IgE-producing human myeloma NGE-41 and mouse myeloma MPC11 (purchased from Dainippon Pharmaceutical) and the cells used as monolayer cells were monkey kidney-derived Vero cells (purchased from Flow Lab. Inc., USA) and swine kidney-derived PS cells (available from Kyoto University, Institute for Virus Research).

With the myelomas, incubation and cell proliferation ratio measurement were conducted in the same manner as in Example 1.

With the monolayer cells, each medium prepared was distributed in 1 ml/well portions into the wells of a 24-well multidish and then a suspension of Vero cells or PS cells ($5\times10^5$ to $1.5\times10^6$ cells/ml) was distributed in 0.1-ml portions thereinto. After 5 days of incubation in a 5% $CO_2$ incubator at 37° C., the supernatant was discarded, 0.25% trypsin was newly added in 1-ml portions and the cells were scraped off from the multidish to give a cell suspension, which was then subjected to cell counting using a Coulter counter.

TABLE 2

| | Salting out with ammonium sulfate[*1] | Addition of ITES | Cell line | | | |
|---|---|---|---|---|---|---|
| | | | NGE-41 | MPC-11 | Vero | PS |
| Fetal bovine serum | Not done | − | 11.0 | 13.0 | 5.3 | 3.7 |
| | | + | — | — | 4.3 | 3.6 |
| | Done | − | 8.0 | 11.0 | 3.7 | 3.7 |
| | | + | 10.5 | 13.0 | 3.9 | 3.6 |
| Neonatal bovine serum | Not done | − | 7.0 | 15.0 | — | — |
| | | + | 11.0 | 21.0 | — | — |
| | Done | − | 5.5 | 11.0 | — | — |
| | | + | 7.0 | 21.0 | — | — |
| Calf serum | Not done | − | 7.0 | 14.0 | 3.2 | 3.0 |
| | | + | 9.0 | 15.0 | 3.4 | 3.4 |
| | Done | − | 6.0 | 8.0 | 3.6 | 4.3 |
| | | + | 9.0 | 13.0 | 3.9 | 4.1 |
| Adult bovine serum | Not done | − | Death (8.0)[*2] | 3.0 (9.0) | Death | Death |
| | | + | Death (9.0) | 3.0 (11.0) | Death | Death |
| | Done | − | 5.0 (5.0) | 4.0 (5.0) | 2.8 | 2.8 |
| | | + | 7.0 (9.0) | 10.0 (14.0) | 4.0 | 2.5 |
| Equine serum | Not done | − | 6.5 | 17.0 | 3.4 | 3.2 |
| | | + | 7.0 | 19.0 | 3.6 | 3.6 |
| | Done | − | 4.5 | 11.0 | 3.5 | 3.6 |
| | | + | 5.0 | 15.0 | 3.7 | 3.8 |
| Ovine serum | Not done | − | 5.0 | 5.0 | 4.0 | 3.6 |
| | | + | 5.0 | 10.0 | 3.9 | 3.4 |
| | Done | − | 5.0 | 5.0 | 3.8 | 4.2 |
| | | + | 7.5 | 10.0 | 3.9 | 4.6 |
| Bovine serum albumin | Not done | − | 3.0 | 4.0 | 2.5 | 2.5 |
| | | + | 5.0 | 16.0 | 2.5 | 3.4 |
| No addition | Not done | − | 2.5 | 2.5 | 2.2 | 2.0 |
| | | + | 2.5 | 4.0 | 2.5 | 3.3 |

The values in the table each indicates the cell proliferation rate.
[*1] Fraction salted out by 45–80% or 57–70% ammonium sulfate saturation
[*2] The values in the parentheses are for the cases where an adult bovine serum lot lacking in cytoxicity was used.

For the myeloma cell lines, sera other than ovine serum, when added alone after salting out, each gave a reduced cell proliferation rate as compared with the rate before salting out. However, when added in combination with ITES, each serum fraction gave a cell proliferation rate comparable to or rather higher than the cell proliferation rate obtained with the corresponding serum before salting out.

In the case of ovine serum, the single addition of the serum before salting out and the ammonium sulfate-salted out fraction resulted in little difference in cell proliferation rate. Combined addition of the ammonium sulfate-salted out fraction with ITES increased the cell proliferation rate to a considerable extent and, in some kinds of cells, good cell proliferation rates were obtained.

On the other hand, for the monolayer cells, the use of the ammonium sulfate-salted out fractions of sera other than fetal bovine serum gave cell proliferation rate values comparable to or slightly higher than the values obtained with the sera before salting out. In particular, the addition of the ammonium sulfate-salted out fractions in combination with ITES gave good cell proliferation rates.

As in Example 1, a bovine serum showing cytotoxicity was freed of toxic substances by salting out with ammonium sulfate.

As compared with bovine serum albumin, higher cell proliferation rates were obtained, in both the cell lines, with the ammonium sulfate-salted out fractions. The differences were significant in particular when the fractions were added together with ITES. Thus, also in the monolayer cells, good cell growth promoting effect was attained by adding various salted-out serum fractions in combination with ITES.

EXAMPLE 3

(Effect of inactivating agents on contamined microorganisms in serum)

It is a matter of concern that animal sera are sometimes contaminated with microorganisms, mainly animal-derived viruses and mycoplasmas. If such contaminated sera are used as cell growth promoting substances, cells may be infected with such microorganisms, in particular those filtrable microorganisms, whereby serious obstacles such as cell growth inhibition and death of cells will be encountered.

However, it is impossible to sterilize sera by heating. For the time being, there is no alternative but to sterilize sera by bacterial filtration. Filtrable microorganisms such as viruses cannot be removed by such method, however. To cope with this situation, an inactivating agent was sought which could inactivate microorganisms occurring in serum completely but would not inhibit cell growth promoting substances contained in serum.

Mycoplasma, vaccinia virus and Japanese encephalitis virus were separately suspended, as contaminant microorganisms, in microorganism-free, normal calf serum having good cell growth promoting effect. The concentrations of microorganisms were: $10^7$ PFU/ml for mycoplasma, $10^8$ ICID$_{50}$/ml for vaccinia virus and $10^6$ TCID$_{50}$/ml for Japanese encephalitis virus. Following addition of each of the inactivating agents given in Table 3 to each microorganism suspension in serum, inactivation treatment was performed under varied conditions. After inactivation treatment, each serum was dialyzed against physiological saline overnight to thereby remove the inactivating agent, and then the remaining microorganisms in each serum were counted and compared with the count of microorganisms remaining in the serum treated in the same manner without adding the inactivating agents.

Furthermore, these inactivating agents were examined for their effect on cell growth promoting substances. Thus, each inactivating agent was added to normal calf serum, followed by inactivation treatment under the same conditions as mentioned above. Part of the serum was dialyzed against physiological saline overnight and the dialyzate was used as the serum before salting out. The remaining serum portion was salted out by 57–80% ammonium sulfate saturation and then dialyzed against physiological saline overnight and the dialyzate was used as the ammonium sulfate-salted out fraction. Each serum material was added to DME/F12 medium to a concentration of 5 mg/ml as protein, either alone or in combination with ITES, followed by incubation of NGE-41 cells by the procedure of Example 1. The cell proliferation rates thus obtained were compared.

The results obtained in the above are shown in Table 3.

TABLE 3

| Inactivating agent | concentration (vol. %) | Treatment temperature (°C.) | duration of treatment (days) | Cell proliferation rate*[1] Serum before salting out ITES − | Cell proliferation rate*[1] Serum before salting out ITES + | Cell proliferation rate*[1] Ammonium sulfate-salted out fraction ITES − | Cell proliferation rate*[1] Ammonium sulfate-salted out fraction ITES + | Microorganism inactivating effect Mycoplasma Number of colonies ($log_{10}$PFU/ml) | Microorganism inactivating effect Vaccinia virus Tissue culture infectious dose ($log_{10}$TCID$_{50}$/ml) | Microorganism inactivating effect Japanese encephalitis virus Tissue culture infectious dose ($log_{10}$TCID$_{50}$/ml) |
|---|---|---|---|---|---|---|---|---|---|---|
| Liquid ethylene oxide | 1.0 | 5 | 7 | 4.5 | 4.7 | 4.7 | 5.0 | <0 | <0 | <0 |
|  | 3.0 | 5 | 7 | 4.0 | 4.0 | 4.8 | 4.8 | — | — | — |
|  | 1.5 | 5 | 3 | — | — | 3.8 | 5.2 | <0 | <0 | <0 |
|  | 1.5 | 18–22 | 3 | — | — | 3.2 | 4.8 | <0 | <0 | <0 |
| Glutaraldehyde | 0.1 | 5 | 3 | — | — | 2.5 | 4.2 | 6 | <0 | <0 |
|  | 0.1 | 18–22 | 3 | — | — | 2.9 | 4.5 | 6 | <0 | <0 |
| Phenol | 0.5 | 5 | 7 | 5.0 | 5.3 | 4.0 | 4.3 | 6.5 | 8 | 5 |
| Formalin | 0.1 | 5 | 7 | Death | Death | Death | Death | — | — | — |
| Sodium azide | 0.1 | 5 | 7 | 1.3 | 1.3 | 1.3 | 2.0 | 7 | 8 | 6 |
| Chlorhexidine | 0.007 | 5 | 6 | — | — | 1.0 | 1.0 | — | — | — |
| Sodium hypochlorite | 0.02 | 5 | 6 | — | — | 3.7 | 5.0 | — | 7 | 6 |
| No addition | — | 5 | 7 | 5.0 | 5.5 | 4.5 | 5.0 | 7 | 8 | 6 |

*[1]Cell proliferation rate in cell line NGE-41.
Sera or their fractions were use at the concentration of 5 mg/ml.

EXAMPLE 4

To 1 liter of adult bovine serum, there was added dropwise 15 ml of liquid ethylene oxide with adequate stirring. After addition, the mixture was allowed to stand at 5° C. for 5 days. Thereto was added portionwise 350 g of ammonium sulfate. After dissolution of the ammonium sulfate, the solution was allowed to stand at 5° C. overnight. The resulting precipitate was removed by centrifugation (9,000×g, 20 minutes). To the supernatant thus obtained, there was added portionwise 140 g of ammonium sulfate. After dissolution of the ammonium sulfate, the solution was allowed to stand as it was at 5° C. overnight. The precipitate formed was collected by centrifugation (9,000×g, minutes) and dissolved in about 100 ml of physiological saline. The solution was placed in a dialyzing membrane (Visking) and dialyzed against 15 liters of physiological saline at 5° C. overnight. The dialyzing fluid was then replaced with fresh 15 liters of physiological saline and the dialysis was further continued at 5° C. overnight.

The dialyzate was taken out and adjusted to a protein content of 60 mg/ml with physiological saline and filtered for removal of bacteria through a membrane filter (0.22 μm, Millipore) to give 500 ml of a composition for animal cell culture.

To 300 ml of a basal medium composed of DME/F12 (1:1), there was added the above composition for cell culture to a concentration of 3 mg/ml as protein, followed by further addition of 3 mg of insulin, 6 mg of transferrin, 36.6 μg of ethanolamine and 1.4 μg of sodium selenate and the subsequent bacterial filtration through a membrane filter (Millipore). There was thus obtained a medium for cell cultivation.

EXAMPLE 5

A swine serum fraction obtained by salting out with ammonium sulfate was examined for cell growth promoting activity. The results obtained are shown in Table 4. Thus, 7.5 ml of liquid ethylene oxide was added dropwise to 1 liter of swine serum with good stirring. The mixture was allowed to stand at 25° C. for 2 days. To each of 3 lots (A, B, C) obtained in this manner, there was added portionwise 350 g of ammonium sulfate. The resultant solution was allowed to stand at 5° C. overnight. The resultant precipitate was removed by centrifugation (9000 xg, 20 minutes). To the supernatant obtained was further added portionwise 140 g of ammonium sulfate. After dissolution of the ammonium sulfate, the solution was allowed to stand at 5° C. overnight. The resultant precipitate was collected by centrifugation (9000 xg, 20 minutes) and then dissolved in about 100 ml of physiological saline. This solution was placed in a dialyzing membrane (Visking) and dialyzed against 15 liters of physiological saline at 5° C. overnight. The dialyzing fluid was then exchanged for fresh 15 liters of physiological saline and the dialysis was further conducted at 5° C. overnight.

The dialyzate was taken out and the protein concentration was adjusted to 60 mg/ml with physiological saline. The dialyzate was filtered through a membrane filter (0.22 μm; Millipore) for removal of bacteria. Thus was obtained 500 ml of a composition for cell cultivation.

The above composition was added, in an amount of 2 mg/ml, to Iscove/F12 basal medium, together with ITES and, following the procedure of Example 1, the cell growth promoting effect was investigated in a total of 6 myeloma and hybridoma cell lines. As controls for comparison with respect to cell growth promoting activity, there were used fetal bovine serum and ammonium sulfate fractions from calf serum and adult bovine serum. No difference in cell growth promotion was noted among the 3 lots of swine serum-drived ammonium sulfate fraction, and said lots were comparable or rather superior in cell growth promoting activity to ammonium sulfate-salted out fractions from calf and adult bovine sera.

TABLE 4

| Material | Cell I-63 | CEA | HS-11 | MPC-11 | NGE-41 | NGE-44 |
|---|---|---|---|---|---|---|
| Fetal bovine serum | 100* | 100 | 100 | 100 | 100 | 100 |
| Ammonium sulfate-salted out fraction from Swine serum | | | | | | |

TABLE 4-continued

| Material | Cell | | | | | |
|---|---|---|---|---|---|---|
| | I-63 | CEA | HS-11 | MPC-11 | NGE-41 | NGE-44 |
| A | 72 | 94 | 70 | 96 | 79 | 141 |
| B | 84 | 98 | 80 | 111 | 86 | 136 |
| C | 66 | 60 | 67 | 76 | 75 | 135 |
| Fetal bovine serum (obtained in Example 2) | 61 | 88 | 73 | 69 | 77 | 111 |
| Adult bovine serum (obtained in Example 2) | 80 | 102 | 78 | 93 | 84 | 112 |

*The values in the table each indicates the relative cell growth promoting activity (the activity of fetal bovine serum being 100) after 3 subcultures in each medium.
Cells were cultured in Iscove/F12 with fetal bovine serum (6 mg/ml) or with each ammonium sulfate-salted out fraction (2 mg/ml) plus ITES

EXAMPLE 6

(Experiments in which the composition for animal cell culture according to the invention was applied to various basal media)

Generally, the growth of cells largely depends on the basal medium and the kind of proliferation promoting additive. Therefore, a search was conducted to identify which basal media could be used with the composition of the present invention to achieve the maximum growth promoting effect.

In the medium search, 14 media were used, namely Serumless Medium (GIBCO; liquid; Neuman & Tytell formulation) and the following 13 publicly available basal media: Iscove [Boehringer Mannheim-Yamanouchi; power; made ready for use in situ (i.e. dissolved in water followed by bacterial filtration in accordance with the directions for use; the same shall apply hereinbelow)], F12 (Nissui; powder; made ready for use in situ); MEM, William-D, William-E, Waymouth-MB752/1, Fischer, RPMI-1640, 199 (each from GIBCO; liquid); DME, NCTC-109, McCoy 5A and alpha-MEM (each from MAB; liquid). Cell proliferation experiments were conducted using the above 14 media either alone or in combination with one another. Thus, the composition of the invention as produced by the procedure of Example 4 was added, in an amount of 2 mg/ml and together with ITES, to each of the 14 media and 91 mixed media prepared by mixing two of the media in a 1:1 ratio (105 media in total). Cells were cultured following the procedure of Example 1 and the cells were counted for the 3rd subculture.

The cells used were I-63 (mouse hybridoma), CEA (mouse hybridoma) and HL15-10 (human hybridoma).

The results obtained are shown in Table 5.

TABLE 5

| basal medium*[1] | a | b | c | d | e | f | g | h | i | j | k | l | m | n | *[2] |
|---|---|---|---|---|---|---|---|---|---|---|---|---|---|---|---|
| | | | | cell: HL15-10 | | | | | | | | | | | |
| a ISCOVE | | 3 | 2 | 1 | 1 | 1 | 1 | 1 | 1 | 1 | 2 | 1 | 2 | 3 | |
| b F12 | 3 | | 2 | 1 | 1 | 1 | 1 | 1 | 1 | 1 | 1 | 1 | 2 | 2 | |
| c DME | 2 | 2 | | 1 | 1 | 1 | 1 | 1 | 1 | 1 | 1 | 1 | 1 | 1 | |
| d NCTC-109 | 1 | 1 | 1 | | 1 | 1 | 1 | 1 | 1 | 1 | 1 | 1 | 1 | 1 | |
| e McCoy-5A | 1 | 1 | 1 | 1 | | 1 | 1 | 1 | 1 | 1 | 1 | 1 | 1 | 2 | |
| f MEM | 1 | 1 | 1 | 1 | 1 | | 1 | 1 | 1 | 1 | 1 | 1 | 1 | 2 | |
| g alpha-MEM | 1 | 1 | 1 | 1 | 1 | 1 | | 1 | 1 | 1 | 1 | 1 | 1 | 1 | |
| h William-D | 1 | 1 | 1 | 1 | 1 | 1 | 1 | | 1 | 1 | 1 | 1 | 1 | 1 | |
| i William-E | 1 | 1 | 1 | 1 | 1 | 1 | 1 | 1 | | 1 | 1 | 1 | 1 | 1 | |
| j Waymouth MB | 1 | 1 | 1 | 1 | 1 | 1 | 1 | 1 | 1 | | 1 | 1 | 1 | 1 | |
| k Fisher | 2 | 1 | 1 | 1 | 1 | 1 | 1 | 1 | 1 | 1 | | 1 | 1 | 1 | |
| l RPMI-1640 | 1 | 1 | 1 | 1 | 1 | 1 | 1 | 1 | 1 | 1 | 1 | | 1 | 2 | |
| m 199 | 2 | 2 | 1 | 1 | 1 | 1 | 1 | 1 | 1 | 1 | 1 | 1 | | 2 | |
| n Serumless Medium | 3 | 2 | 1 | 1 | 2 | 2 | 1 | 1 | 1 | 1 | 2 | 2 | | 1 | |
| Ref. fetal bovine serum | 3 | 2 | 1 | 1 | 1 | 1 | 2 | 1 | 1 | 1 | 1 | 1 | 1 | 1 | |
| Ref. bovine serum albumin | 1 | 1 | 1 | 1 | 1 | 1 | 1 | 1 | 1 | 1 | 1 | 1 | 1 | 1 | | cell: CEA

TABLE 5-continued

| basal medium[*1] | a | b | c | d | e | f | g | h | i | j | k | l | m | n | [*2] |
|---|---|---|---|---|---|---|---|---|---|---|---|---|---|---|---|
| a ISCOVE | 1 | 2 | 2 | 2 | 2 | 2 | 2 | 2 | 2 | 0 | 2 | 2 | 1 | 3 | |
| b F12 | 2 | 2 | 2 | 2 | 1 | 1 | 1 | 2 | 2 | 0 | 1 | 2 | 2 | 3 | |
| c DME | 2 | 2 | 0 | 1 | 0 | 1 | 1 | 1 | 0 | 0 | 1 | 0 | 1 | 2 | |
| d NCTC-109 | 2 | 2 | 1 | 0 | 0 | 0 | 0 | 1 | 1 | 0 | 0 | 0 | 0 | 2 | |
| e McCoy-5A | 2 | 1 | 1 | 0 | 0 | 0 | 0 | 1 | 0 | 0 | 0 | 0 | 0 | 2 | |
| f MEM | 2 | 1 | 1 | 0 | 0 | 0 | 2 | 1 | 1 | 0 | 0 | 0 | 1 | 2 | |
| g alpha-MEM | 2 | 1 | 1 | 0 | 1 | 2 | 1 | 2 | 2 | 0 | 1 | 1 | 1 | 2 | |
| h William-D | 2 | 2 | 1 | 1 | 0 | 1 | 2 | 1 | 1 | 0 | 0 | 0 | 1 | 2 | |
| i William-E | 2 | 2 | 0 | 1 | 0 | 1 | 2 | 1 | 0 | 0 | 0 | 0 | 1 | 2 | |
| j Waymouth MB | 0 | 0 | 0 | 0 | 0 | 0 | 0 | 0 | 0 | 1 | 1 | 0 | 0 | 0 | |
| k Fisher | 2 | 1 | 1 | 0 | 0 | 0 | 1 | 0 | 0 | 1 | 0 | 0 | 0 | 0 | |
| l RPMI-1640 | 2 | 2 | 0 | 0 | 0 | 0 | 1 | 0 | 0 | 0 | 0 | 0 | 0 | 1 | |
| m 199 | 1 | 2 | 1 | 0 | 0 | 1 | 1 | 1 | 1 | 0 | 0 | 0 | 0 | 2 | |
| n Serumless Medium | 3 | 3 | 2 | 2 | 2 | 2 | 2 | 2 | 2 | 0 | 0 | 1 | 2 | 0 | |
| Ref. fetal bovine serum | 3 | 2 | 2 | 1 | 2 | 2 | 2 | 2 | 3 | 2 | 0 | 1 | 1 | 1 | |
| Ref. bovine serum albumin | 1 | 1 | 1 | 0 | 0 | 0 | 1 | 1 | 1 | 1 | 0 | 0 | 0 | 0 | |
| cell: I-63 | | | | | | | | | | | | | | | |
| a ISCOVE | 2 | 3 | 2 | 1 | 2 | 3 | 2 | 2 | 2 | 1 | 2 | 3 | 2 | 3 | |
| b F12 | 3 | 1 | 1 | 1 | 1 | 1 | 1 | 1 | 1 | 1 | 1 | 1 | 1 | 2 | |
| c DME | 2 | 1 | 1 | 1 | 1 | 1 | 1 | 1 | 1 | 1 | 1 | 1 | 1 | 1 | |
| d NCTC-109 | 1 | 1 | 1 | 1 | 1 | 1 | 1 | 1 | 1 | 1 | 1 | 1 | 1 | 1 | |
| e McCoy-5A | 2 | 1 | 1 | 1 | 1 | 1 | 1 | 1 | 1 | 1 | 1 | 1 | 1 | 1 | |
| f MEM | 3 | 1 | 1 | 1 | 1 | 1 | 1 | 1 | 1 | 1 | 1 | 1 | 1 | 1 | |
| g alpha-MEM | 2 | 1 | 1 | 1 | 1 | 1 | 1 | 1 | 1 | 1 | 1 | 1 | 1 | 3 | |
| h William-D | 2 | 1 | 1 | 1 | 1 | 1 | 1 | 1 | 1 | 1 | 1 | 1 | 1 | 1 | |
| i William-E | 2 | 1 | 1 | 1 | 1 | 1 | 1 | 1 | 1 | 1 | 1 | 1 | 1 | 1 | |
| j Waymouth MB | 1 | 1 | 1 | 1 | 1 | 1 | 1 | 1 | 1 | 1 | 1 | 1 | 1 | 1 | |
| k Fisher | 2 | 1 | 1 | 1 | 1 | 1 | 1 | 1 | 1 | 1 | 1 | 1 | 1 | 1 | |
| l RPMI-1640 | 3 | 1 | 1 | 1 | 1 | 1 | 1 | 1 | 1 | 1 | 1 | 1 | 1 | 1 | |
| m 199 | 2 | 1 | 1 | 1 | 1 | 1 | 1 | 1 | 1 | 1 | 1 | 1 | 1 | 1 | |
| n Serumless Medium | 3 | 2 | 1 | 1 | 1 | 1 | 3 | 1 | 1 | 1 | 1 | 1 | 1 | 1 | |
| Ref. fetal bovine serum | 3 | 2 | 1 | 2 | 2 | 2 | 2 | 2 | 2 | 1 | 1 | 1 | 1 | 1 | |
| Ref. bovine serum albumin | 1 | 1 | 1 | 1 | 1 | 1 | 1 | 1 | 1 | 1 | 1 | 1 | 1 | 1 | |

[*1]To the individual basal media a to n (in the table, surrounded by ☐) and 1:1 mixed basal media, there was added the composition of the invention from bovine serum, in an amount of 2 mg/ml, together with ITES.
[*2]Each value in the table indicates the score assigned, according to the range conversion given below, to the number of cells after 3 subcultures in each medium:

For HL15-10:
0: Death
1: less than $50 \times 10^4$ cells/ml
2: 50 to $100 \times 10^4$ cells/ml
3: more than $100 \times 10^4$ cells/ml For CEA
0: Death
1: less than $15 \times 10^4$ cells/ml
2: 15 to $25 \times 10^4$ cells/ml
3: more than $25 \times 10^4$ cells/ml For I-63
0: Death
1: less than $15 \times 10^4$ cells/ml
2: 15 to $30 \times 10^4$ cells/ml
3: more than $30 \times 10^4$ cells/ml.

Fetal bovine serum: As a control, fetal bovine serum was added to each individual basal medium to a concentration of 10%.
Bovine serum albumin: As a control, bovine serum albumin was added to each individual basal medium to a concentration of 5 mg/ml, together with ITES.

With regard to the mixed media, on the other hand, Iscove- or Serumless Medium-containing mixed media allowed good proliferation of I-63 and HL15-10. In CEA, few mixed media afforded good proliferation. Among others, Iscove and Serumless Medium produced the desired mixture effect with a number of other media. In view of factors such as cell proliferation, general usefulness, and the like, it was generally considered that mixtures of basal media produced a much better growth enhancement effect than did the use of a single medium. Preferred mixed media are, for example, Iscove/F12, Iscove/Serumless Medium, F12/Serumless Medium, and alpha-MEM/Serumless Medium.

Next, the effect of the mixing ratio between two media was studied for the combination of Iscove and F12. Thus, Iscove (Boehringer Mannheim-Yamanouchi) and F12 (Nissui) were mixed in the ratios of 1:0, 1:1, 1:1, 1:3, 1:4, 1:7, 1:15 and 0:1, and, following addition of 2 mg/ml of the composition of the invention as obtained in Example 4 and ITES, cultivation was performed in these mixed media. After three subcultures, the cells were counted. The cell lines used were NGE-44 (derived from the above-mentioned NGE-41 by adaptation to a medium containing said composition), CEA (mouse hybridoma) and I-63 (mouse hybridoma).

The results obtained are illustrated in FIG. 1. In all the cell lines used, the mixed media each brought about fairly good cell proliferation as compared with the single medium Iscove or F12. In the Iscove-to-F12 mixing ratio of 1:1 to 1:7, the cell proliferation was good, and it was concluded that the mixing ratio between the media in preparing mixed media supplemented with the composition according to the invention can be selected within a fairly wide range.

EXAMPLE 7

(Effect of the composition for animal cell culture according to the invention in roller bottle culture)

The applicability of the composition of the present invention to roller bottle culture was investigated in connection with the kind of basal medium employed. As the media, there were used Iscove/F12 (1:1) and DME/F12 (1:1), each supplemented with the composition obtained in Example 4 (2 mg/ml) and ITES. I-63 cells were cultured in a 1-liter jar fermenter (Mitsuwa Rika model KMJ-2). In a control run, a suspension of the same cells were distributed in about 6-ml portions into 25-cm$^2$ tissue culture flasks (Falcon) and stationary culture was conducted. The results thus obtained are shown in FIG. 2.

Figure 2:
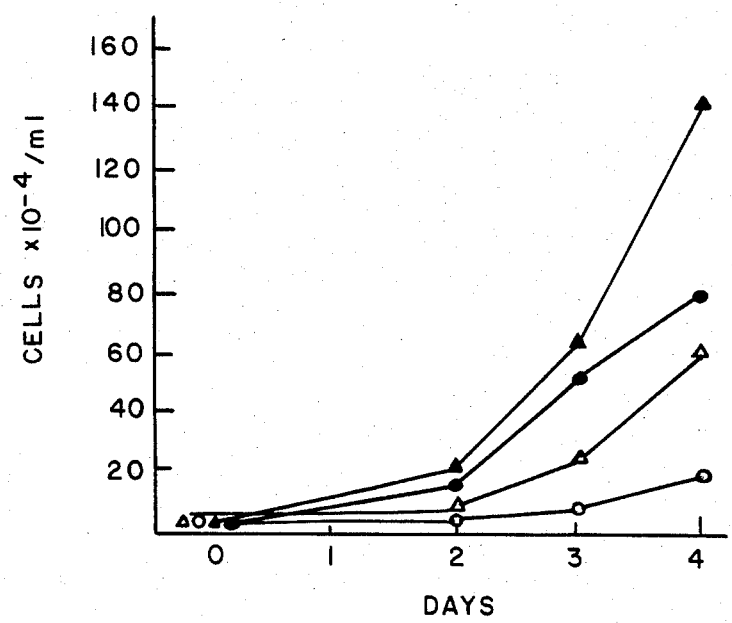
FIG. 2 shows the effect of the composition of the invention as produced in Example 7 in stationary culture and in jar fermenter culture (    and    indicating the results of jar fermenter culture using Isove/F12 and DME/F12, respectively and    and    indicating the results of stationary culture using Iscove/F12 and DME/F12, respectively).

As is evident from FIG. 2, the composition according to the present invention exhibited excellent cell proliferation promoting effect in both the roller bottle culture and stationary culture.

In roller bottle culture, the Iscove/F12 mixed medium gave excellent results, with the final number of cells amounting to $80 \times 10^4$ cells.

What is claimed is:

1. A method of producing a mammalian serum-originated growth factor-containing composition for animal cell cultivation, which method comprises subjecting a mammalian serum to treatments comprising:
   (a) contacting the serum with an effective virus and mycoplasma inactivating amount of an inactivating agent selected from the group consisting of $C_2$ to $C_4$ alkenyl oxides, and $C_2$ to $C_5$ dialdehydes,
   (b) salting out said serum first with an aqueous inorganic salt solution at a lower concentration limit of not less than 55% saturation and second with an aqueous inorganic salt solution at an upper concentration limit of not higher than 70% saturation,
   (c) desalting the precipitate produced by the second salting out solution and
   (d) recovering said mammalian serum-originated growth factor-containing composition from said precipitate.

2. The method according to claim 1, wherein said inactivating agent is liquid ethylene oxide, and said desalting is conducted by dialysis.

3. The method according to claim 2, wherein the liquid ethylene oxide treatment is conducted at a concentration of from about 0.1 to 5% by volume at a temperature range of from about 0° C. to 30° C. for from about 1 to 7 days.

4. The method according to claim 1 or 2, wherein the inorganic salt is an ammonium salt.

5. The method according to claim 4, wherein the ammonium salt is an ammonium sulfate.

6. The method according to claims 1 or 2, wherein the step of salting out and desalting are conducted after the step of contacting with the inactivating agent.

7. The method according to claims 1 or 2, wherein the mammalian serum is of adult mammal origin.

8. The method according to claims 1 or 2, wherein the mammalian serum is a member of the group consisting of bovine serum, equine serum, ovine serum, and swine serum.

9. The method according to claim 8, wherein the mammalian serum is bovine serum.

10. The method according to claim 8, wherein the mammalian serum is swine serum.

11. The mammalian serum-originated growth factor-containing composition useful for animal cell cultivation free from contaminant viruses, mycoplasmas, and cytotoxic substances including growth ihibiting substances, antibodies, and other immunoglobulins, said composition being formed by the process of claim 1.

12. A medium for cell cultivation which contains the composition according to claim 11, together with a basal medium.

13. The medium according to claim 12, wherein the composition is added to the basal medium in a concentration of from about 1 to 10 mg/ml.

14. The medium according to claim 12, which further contains one or more trace growth promoting substances selected from the group consisting of insulin, transferrin, ethanolamine and sodium selenate.

15. A method of cultivating mammalian cells which comprises cultivating said cells in the medium according to claim 12.

* * * * *

UNITED STATES PATENT AND TRADEMARK OFFICE
CERTIFICATE OF CORRECTION

PATENT NO.  :  4,654,304
DATED       :  31 March 1987
INVENTOR(S) :  Seijiro Sasai et al.

It is certified that error appears in the above-identified patent and that said Letters Patent are hereby corrected as shown below:

Title Page - Change Assignee from "Takeda Chemical Industries" to ---Director-General of Agency of Industrial Science and Technology---.

Signed and Sealed this

Eighteenth Day of August, 1987

*Attest:*

DONALD J. QUIGG

*Attesting Officer*      *Commissioner of Patents and Trademarks*